United States Patent [19]

Harris et al.

[11] Patent Number: 4,670,258

[45] Date of Patent: Jun. 2, 1987

[54] STORABLE PREPACKAGED AQUEOUS SOLUTIONS OF VANCOMYCIN

[75] Inventors: Thomas M. Harris; Constance M. Harris, both of Nashville, Tenn.

[73] Assignee: Vanderbilt University, Nashville, Tenn.

[21] Appl. No.: 578,848

[22] Filed: Feb. 10, 1984

[51] Int. Cl.$^4$ ............................................. A61K 35/00
[52] U.S. Cl. .................................................. 424/115
[58] Field of Search ........................................ 424/115

[56] References Cited

U.S. PATENT DOCUMENTS 3,067,099 12/1962 McCormick et al. .............. 424/115

OTHER PUBLICATIONS

Chem. Abst., 82-149985a (1975) & 97-56252d (1982).
Harris et al., (1983), J. Am. Chem. Soc., 105:6915-6922.
Williams et al., (1983), J. Am. Chem. Soc., 105:1332-1339.
Brown et al., Mol. Pharmacol. (1975), 11(2):119-125.
Harris and Harris, J. Am. Chem. Soc. (1982) 104(15):4293-4295.
Nieto and Perkins, (1971), Biochem. J. 123:789-803.
Perkins, (1982), Pharmac. Ther. 16:181-197.
Mann et al., (1977), Am. J. Hosp. Pharm., 28:760-763.
Wamberg et al., (1980), Arch. Pharm. Chemi., Sci. Ed. 8:1-4.
Nieto and Perkins, (1972), Biochem. J. 126:139-149.
Harris et al., (1985), J. Antibiotics 38(1):51-57.
Harris and Harris (1982), J. Am. Chem. Soc., 104:4293-4295.

*Primary Examiner*—Stanley J. Friedman
*Attorney, Agent, or Firm*—Tilton, Fallon, Lungmus & Chestnut

[57] ABSTRACT

Vancomycin and other vancomycin-type antibiotics, which contain asparagine, as the third residue are prepared in storable prepackaged solutions. The antibiotics are made storage-stable by the incorporation of a short chain peptide of the class binding to vancomycin. The solutions may be used for intravenous, oral, or peritoneal administration, and also in diagnostic uses.

9 Claims, No Drawings

STORABLE PREPACKAGED AQUEOUS SOLUTIONS OF VANCOMYCIN

GRANT REFERENCE

This invention was develiped in part under NIH Grant No. GM 23593.

FIELD OF INVENTION

The field of this invention is the packaging and storing of aqueous solutions of antibiotics, especially aqueous solutions of vancomycin or other vancomycin-type antibiotics which are subject to decomposition during storage in aqueous solutions. The prepackaged aqueous solutions may be for intravenous, oral, or peritoneal use.

BACKGROUND AND PRIOR ART

Vancomycin is a known antimicrobial which can be used clinically in aqueous solutions for intravenous or oral administration and in peritoneal dialysis fluids. It is particularly effective against Staphylococcus and is therefore employed to combat staphylococcal infections which are resistant to penicillin. See Geraci and Hermans (1983), *Mayo Clin. Proc.* 58: 88–91. It is administered intravenously for treatment of systemic infections. Its oral use is primarily for staphylococcal ileocolitis and antibiotic-induced enterocolitis associated with *Clostridium difficile*. It has also been shown to be useable in peritoneal dialysate solutions. See Sewell and Golper (1982), *Antimicrobial Agents and Chemotherapy* 21 (3): 528–529.

Vancomycin may be produced by the process described in U.S. Pat. No. 3,067,099. It is available commercially from Eli Lilly & Company, Indianapolis, Ind. under the product name "Vancocin". It is commonly marketed and used in salt form, that is, as vancomycin hydrochloride.

The structures of vancomycin and other vancomycin-type antibiotics have been widely studied. The definitive structure of vancomycin is believed to be shown in two recent publications: Williamson and Williams (1981), *J. Am. Chem. Soc.* 103: 6580–6585; and Harris and Harris (1982), *J. Am. Chem. Soc.* 104: 4293–4295. The structure is a linear heptapeptide containing an actinoidinic acid and a vancomycinic acid. As reported in the latter reference, the structure of vancomycin includes an asparagine residue which is subject to rearrangement. The mechanism of this rearrangement has been investigated (Harris, Kopecka and Harris (1983), *J. Am. Chem. Soc.* 105:6915–6922). The rearrangement product lacks antibiotic activity (Marshall (1965), *J. Med. Chem.* 8: 18–22).

The preferred clinical practice is to use the vancomycin solution within 24 hours after preparation. However, it is known that aqueous solutions of vancomycin can be stored for several weeks at refrigeration temperatures (viz. 5° C.), but that potency is lost and autogenous pH changes occur either at room temperature or after prolonged storage under refrigeration. See Mann, Coleman,, and Boylan (1971), *Am. J. Hosp. Pharm.* 28: 760–763; and Wamberg, Nielsen, and Scheibel (1979), *Arch. Pharm. Chem. Sci. Ed.* 8: 1–4.

It is known that vancomycin-type antibiotics form a complex in aqueous solution, particularly with peptides terminating in D-alanyl-D-alanine. The classes of dipeptides and tripeptides binding in aqueous solution to vancomycin and other vancomycin type antibiotics are known. See Nieto and Perkins (1971), *Biochem. J.* 123: 789–803; and Perkins (1982), *Pharmac. Ther.* 16: 181–197.

SUMMARY OF INVENTION

The structural requirements for peptide binding to the antibiotic have been studied extensively; this invention involves the discovery that peptide-binding to vancomycin and related antibiotics containing the asparagine residue stabilizes these antibiotics against rearrangement of the asparagine residue to an isoaspartate and consequently protects against loss of antibiotic activity. Prior to the present invention there has been no suggestion that such binding produced a stabilizing effect on the vancomycin. By employing at least one mole of the stabilizing peptide per mole of the vancomycin, the storage stability of prepackaged aqueous solutions of vancomycin can be greatly improved. Even for long term storage, refrigeration is not required to maintain adequate potency. This invention therefore permits the preparation of storable prepackaged intravenous solutions of vancomycin, as well as prepackaged solutions for other uses, such as for oral administration, or for use as peritoneal dialysates.

DETAILED DESCRIPTION

The vancomycin for use in practicing the present invention can be in the standard commercial form of vancomycin hydrochloride. This product is available from Eli Lilly & Company, Indianapolis, Ind., being sold under the trademark name "Vancocin". In alternative embodiments, other vancomycin-type antibiotics can be used. The general class is vancomycin-type antibiotics which are unstable on long storage at room temperature in aqueous solutions, and which bind to peptides in aqueous solution. The short chain polypeptides which can be used in practicing the present invention are those which are known to have a binding affinity for vancomycin. Such polypeptides are described in Nieto and Perkins (1971), *Biochem. J.* 123: 789–803; and Perkins (1982), *Pharmac. Ther.* 16: 181–197. The preferred polypeptides are those containing from 2 to 3 amino acid residues. Further, the preferred peptides are those containing terminal D-alanyl-D-alanine. However, other terminal peptide groups may be present which bind to the asparagine residue of the vancomycin or other vancomycin-type antibiotic. The specifically preferred stabilizing peptides are:

1. Dipeptides

Ac-D-ala-D-ala
Ac-gly-D-ala
Ac-D-leu-D-ala
Ac-D-ser-D-ala
Ac-D-glu-D-ala
General form: Acyl-D-aminoacid(or gly)-D-aminoacid 2. Tripeptides α,ε-DiAc-L-lys-D-ala-D-ala
α-Ac-L-lys-D-ala-D-ala
Ac-L-ala-D-ala-D-ala
Ac-L-ala-D-glu-D-ala
General form: Acyl-L-aminoacid(or gly)-D-aminoacid(or gly)-D-aminoacid In all cases the C-terminal aminoacid will have a free carboxyl group and the N-terminus will be acylated on the α-amino group.

Polypeptides for use as binding agents can be purchased from Serva Biochemicals, Garden City Park, N.Y. (α,ε-DiAc-L-lys-D-ala-D-ala) or obtained by custom synthesis from such companies as Serva, Vega Biochemicals (Tucson, Ariz.) or Chemical Dynamics Corp. (South Plainfield, N.J.). They can also be synthesized by literature methods (Nieto and Perkins (1971) *Biochemical J.* 123: 789–803).

In general, the desired stabilizing action is obtained by using at least 1 mole of the binding peptide per mole of the vancomycin or other vancomycin-type antibiotic. Some molar excess of the binding polypeptide is desirable, such as from 1.5 to 2 moles of peptide per mole of antibiotic. However, large excesses of the polypeptide are not needed. In general, it will not be desirable to employ more than two moles of polypeptide per mole of antibiotic.

The concentration of the vancomycin in the aqueous solution will depend on the use to be made of the aqueous solution. In general, the amount of vancomycin used will be below the saturation solubility at refrigeration temperatures (e.g. 5° C.) but in an amount to be antimicrobially-effective for the purpose used. For intravenous administration, the intravenous vehicle may comprise sodium chloride injection 0.9% USP (normal saline) or dextrose 5% USP. These carrier solutions will be prepared as is well known in the art of intravenous fluids. The USP protocols should be followed. While vancomycin may be administered by continuous intravenous drip, it is preferred to administer it in a more concentrated form over a relatively short period of time. For example, the vancomycin may be dissolved in increments of 100 ml or 250 ml of the saline or dextrose solutions. Each dose of vancomycin may range from about 0.5 to 1 gram of vancomycin hydrochloride. Typical concentrations for intravenous administration therefore may range from 500 mg of vancomycin hydrochloride per 250 ml of solution up to 500 mg per 100 ml of solution. In general, for intravenous administration the concentration of the vancomycin (on a vancomycin hydrochloride basis) may range from about 200 to 500 mg of vancomycin per 100 ml of solution.

For oral administration for the treatment of colitis conditions, aqueous solutions of vancomycin can also be used. The concentrations will usually differ from those used for intravenous solutions. For example, for oral administration, the concentration of vancomycin (hydrochloride basis) may range from about 5 to 10 mg of vancomycin per 1 ml of solution.

In peritoneal dialysis solutions, vancomycin may be employed as an antibiotic to control staphylococcal infection. Typical dialysate solutions contain from about 1 to 4% glucose. Other ingredients may also be included. Vancomycin may be added from a concentrated stock solution (>100 μg/ml) to give a final dilute solution, such as from 15 to 50 μg per ml.

In all of the applications of this invention referred to above, it should be understood that the binding polypeptide will be employed in the amount specified above to assure effective stabilizing action. The polypeptides employed should be non-reactive with other components of the solutions, and should be polypeptides which are non-toxic with reference to the particular mode of administration or use. In general, the desirable binding polypeptides are safe for use either intravenously, orally, or in peritoneal fluids. Further, these solutions ordinarily contain no other ingredients besides the vancomycin which would be reactive with the polypeptides.

The solutions may be packaged in conventional plastic or glass containers, as heretofore employed for similar packaging purposes. For example, the intravenous solution containers may be collapsable plastic containers of the size for holding 100 ml or 250 ml, or larger amount of solution. A container size greater than 500 ml will not ordinarily be employed for this purpose. For parenteral administration, the containers will be adapted for connection to intravenous administration sets, either as the primary fluid being administered, or as a supplemental fluid. The administration rate may be controlled by the conventional drip chamber, or by an adjustable rate pump.

The containers for orally administerable fluids, and for peritoneal dialysis fluids will also be the same as those conventionally employed for these purposes. Containers will usually be formed of a suitable plastic. The container sizes may vary from 50 to 1,000 ml, depending on the purpose.

The container for orally administered fluids may be a glass or plastic bottle of 100 to 250 ml size. For peritoneal dialysis the antibiotic-peptide complex could be prepared in concentrated form and packaged in a serum-capped bottle of 2 to 5 ml capacity; the contents could be added by injection to the dialysate solution which would be in a 1-1 plastic bag (e.g. that supplied as Dianeal 137 by Travenol Laboratories, Deerfield, Ill.).

The vancomycin solutions as used for the purpose of the present invention should be sterile as packaged. The sterilization may be achieved prior to, or as part of the packaging process, or subsequent to packaging. For example, the solutions after preparation may be subjected to sterile filtration or in some cases, heat sterilization.

This invention is also applicable to any vancomycin-type antibiotics containing asparagine as the third residue, including chemical derivatives of vancomycin in which the structural modifications have not significantly impaired the peptide-binding properties of the antibiotic, that is, the vancomycin-type antibiotics as a class bind to the same peptides as vancomycin. For example, the aglycone (Marshall (1965) *J. Med. Chem.* 8: 18–22), the dechloro analogs (Harris, Kopecka and Harris (1983) *J. Am. Chem. Soc.* 105: 6915–6922), the iodo derivative (Nieto and Perkins (1971) *Biochem. J.* 123: 773–787), or the N-acetyl derivative (Perkins (1969) *Biochem. J.* 111: 195–205) will be stabilized against rearrangement by binding peptides. In addition, fluorescent and radioactive derivatives such as those used in immunoassays will be stabilized against rearrangement by binding peptides.

The results achieved by the present invention and the manner in which it may be employed in clinical practice are further illustrated by the following examples.

EXAMPLE I

The protection of vancomycin against thermal degradation by binding peptides is illustrated by the following experiment. Solutions containing vancomycin (1 mmol) and peptide (either 1 mmol or 2 mmol) in a total volume of 2 ml (pH 4.1–4.2) were placed in screw-capped test tubes and heated at 80° C. for 17 hr. At the end of the reaction time aliquots of the reaction mixture were analyzed for vancomycin and its degradation products, CDP-I-Major (CDP-I-M) and CDP-I-minor (CDP-I-m), by HPLC (Harris, Kopecka and Harris (1983), *J. Am. Chem. Soc.* 105: 6915–6922). The data are expressed in Table I as $$\% \text{ vancomycin} = \frac{\text{vancomycin}}{\text{vancomycin} + CDP\text{-}I\text{-}M + CDP\text{-}I\text{-}m} \times 100$$

TABLE I

| Additive | % Vancomycin remaining after 17 hr at 80° C. |
|---|---|
| None - unheated control | 92 |
| None - heated | 49 |
| Ac—D-ala-D-ala (1:1, peptide:antibiotic) | 83 |
| Ac—D-ala-D-ala (2:1) | 93 |
| Ac—gly-D-ala (1:1) | 72 |
| Ac—gly-D-ala (2:1) | 80 |
| Di-N—Ac—L-lys-D-ala-D-ala (1:1) | 91 |
| Ac—D-ala-β-ala[1] (1:1) | 58 |

[1]This peptide does not exhibit any measurable binding to vancomycin when studied by UV spectroscopy. The binding constants for the other peptides are of the order of $10^4$ or greater (Perkins (1982) Pharmac. Ther. 16: 182-197).

EXAMPLE II

The protection of antibiotic activity of vancomycin by binding peptide is illustrated by the following experiment. Solutions containing vancomycin (2 mmol) and peptide 4 mmol) in a total volume of 1 ml (pH 4.40) were placed in screw-capped test tubes and heated at 80° C. for 66 h. The residual antibiotic activity was measured by the disc diffusion technique with *B. subtilis* as the test organism (Coller and Gralnick (1977), *J. Clinical Investigation* 60: 302–312; Crossley, Rotschafer, Chern, Mead and Zaske (1980), *Antimicrob. Agents and Chemother.* 17: 654–657). In the cited assay procedure the antibiotic is diluted to approximate a recommended serum level for an antibiotic effectiveness. The data is summarized in Table II.

TABLE II

| Sample | % Activity |
|---|---|
| Vancomycin - unheated | 100 |
| Vancomycin - heated | 25 |
| Vancomycin + Ac—D-ala-D-ala (1:2) - unheated | 100 |
| Vancomycin + Ac—D-ala-D-ala (1:2) - heated | 87 |

EXAMPLE III

Vancomycin-peptide solutions were prepared as in the previous experiments and steam sterilized (15 psi) for 30 min. Antibiotic activity was measured as in Example II. The data is summarized in Table III.

TABLE III

| Sample | % Activity |
|---|---|
| Vancomycin - unheated | 100 |
| Vancomycin - heated | 58 |
| Vancomycin + Ac—D-ala-D-ala (1:1) | 70 |
| Vancomycin + Ac—D-ala-D-ala (2:1) | 81 |
| Vancomycin + Di-N—Ac—L-lys-D-ala-D-ala (1:1) | 98 |

EXAMPLE IV

Solutions suitable for intravenous administration can be prepared as follows:

Vancomycin hydrochloride (500 mg) and Di-N-Ac-L-lys-D-ala-D-ala (122 mg) can be dissolved in sterile water, 5% glucose or saline (pH 4–7.5) and sterilized by filtration. This solution can be injected into 250 ml plastic bags of sterile saline for intravenous administration.

Vancomycin hydrochloride (500 mg) and Di-N-Ac-L-lys-D-ala-D-ala (122 mg) can be dissolved in saline or 5% glucose (250 ml) (pH 4-7.5), sterilized by filtration and placed in sterile plastic bags suitable for intravenous administration.

Other peptides which can be substituted on an equivalent molar basis include:
Ac-D-ala-D-ala
Ac-L-ala-D-ala-D-ala
Ac-D-glu-D-ala

EXAMPLE V

Solutions suitable for oral administration can be prepared as follows:

Vancomycin hydrochloride (1.25 g) and Di-N-Ac-L-lys-D-ala-D-ala (0.30 g) (1:1 molar ratio) can be dissolved in distilled water (115 ml-4 oz.), the pH adjusted to between 4 and 7.5 and the solution sterilized by filtration. Following sterilization the solution can be stored in suitable glass or plastic bottles.

Vancomycin hydrochloride (5 g) and Di-N-Ac-L-lys-D-ala-D-ala (1.22 g) can be dissolved in a mixture of distilled water (400 ml) and strawberry syrup (100 ml). Following sterilization by filtration the solution can be stored in suitable glass or plastic containers.

EXAMPLE VI

Solutions suitable for intraperitoneal administration can be prepared as follows:

Vancomycin hydrochloride (15 mg) and Di-N-Ac-L-lys-D-ala-D-ala, 3.67 mg, 1:1 molar ratio) can be dissolved in 1.5 or 4.25% glucose (5 ml, pH 5.2±0.2) and sterilized by filtration. This solution can be stored in sterile serum-capped vials and added by injection to 1-1 plastic bags of dialysate solution (e.g. Dianeal 137, Travenol Laboratories, Deerfield, Ill.)

We claim:

1. A storable prepackaged solution of an antibiotic selected from the group consisting of vancomycin and related antibiotics, the related antibiotics being further characterized by having asparagine as the third residue thereof from their N-terminus and binding to the same peptides as vancomycin, comprising a sealed container with a sterile aqueous solution therein, said solution having an antimicrobially-effective amount of said antibiotic dissolved therein together with a peptide containing from two to three amino acid residues, said peptide being selected from the group of dipeptides and tripeptides binding to vancomycin in aqueous solution, at least one mole of said binding peptide being present per mole of said antibiotic and said antibiotic being complexed with said peptide.

2. The prepackaged solution of claim 1 in which said antibiotic is vancomycin.

3. The prepackaged solution of claim 1 in which said binding peptide is present in an amount of from 1.5 to 2 moles of peptide per mole of antibiotic.

4. The prepackaged solution of claim 1 in which said binding peptide contains from 2 to 3 amino acid residues.

5. A storable prepackaged solution of vancomycin, comprising a sealed container with a sterile aqueous solution therein, said solution having an antimicrobially-effective amount of vancomycin dissolved therein together with a peptide containing from two to three amino acid residues, said peptide being selected from the class of peptides binding to vancomycin in aqueous solution, from 1.5 to 2 moles of said binding peptide being present per mole of said vancomycin and said vancomycin being complexed with said peptide.

6. A method os stabilizing an antibiotic selected from the group consisting of varicomycin and related antibiotics, the related antibiotics further characterized by having asparagine as the third residue thereof from their N-terminus and binding to the same peptides as vancomycin, comprising mixing an antimicrobially-effective amount of said antibiotic in a sterile aqueous solution with a peptide containing from two to three amino acid residues, said peptides being selected from the group of dipeptides and tripeptides binding to vancomycin in aqueous solution, at least one mole of said binding peptide being present per mole of said antibiotic to complex said antibiotic with said peptide, and sealing said solution in a container.

7. The method of claim 6 wherein said antibiotic is vancomycin.

8. The method of claim 6 wherein said binding peptide is present in an amount of from about 1.5 to about 2 moles of peptide per mole of antibiotic.

9. A method of stabilizing a solution of vancomycin comprising dissolving an antimicrobially-effective amount of vancomycin with a peptide containing from two to three amino acid residues in an aqueous solution, said peptide being selected from the class of peptides binding to vancomycin, from about 1.5 to 2 moles of said binding peptide being present per mole of said vancomycin being complexed with said peptide and sealing said solution in a container.

* * * * *

UNITED STATES PATENT AND TRADEMARK OFFICE
CERTIFICATE OF CORRECTION

PATENT NO. : 4,670,258
DATED : June 2, 1987
INVENTOR(S) : Thomas M. Harris and Constance M. Harris It is certified that error appears in the above-identified patent and that said Letters Patent is hereby corrected as shown below:

In Column 1, line 6, "deviliped" should be --developed--.

Signed and Sealed this

Twenty-seventh Day of October, 1987

Attest:

DONALD J. QUIGG

Attesting Officer

Commissioner of Patents and Trademarks